United States Patent
Holscher et al.

(10) Patent No.: US 10,588,771 B2
(45) Date of Patent: Mar. 17, 2020

(54) WEARABLE SUPPORT STRUCTURE FOR AT LEAST PARTLY RELIEVING A HUMAN BODY DURING LEANING OR BENDING OVER

(71) Applicant: Laevo B.V., Delft (NL)

(72) Inventors: Michael Martinus Holscher, Delft (NL); Bastiaan Bartjan Maat, Delft (NL); Robert Huitema, Delft (NL); Boudewijn Martin Wisse, Delft (NL)

(73) Assignee: Laevo B.V., Delft (NL)

( * ) Notice: Subject to any disclaimer, the term of this patent is extended or adjusted under 35 U.S.C. 154(b) by 99 days.

(21) Appl. No.: 15/557,314

(22) PCT Filed: Mar. 10, 2016

(86) PCT No.: PCT/NL2016/050170
§ 371 (c)(1),
(2) Date: Sep. 11, 2017

(87) PCT Pub. No.: WO2016/148566
PCT Pub. Date: Sep. 22, 2016

(65) Prior Publication Data
US 2018/0049905 A1 Feb. 22, 2018

(30) Foreign Application Priority Data
Mar. 13, 2015 (NL) ...................................... 2014451

(51) Int. Cl.
*A61F 5/00* (2006.01)
*A61F 5/02* (2006.01)
*A61F 5/01* (2006.01)

(52) U.S. Cl.
CPC ................ *A61F 5/026* (2013.01); *A61F 5/01* (2013.01); *A61F 5/028* (2013.01)

(58) Field of Classification Search
CPC .. A61F 5/026; A61F 5/028; A61F 5/02; A61F 5/022; A61F 5/024; A61F 5/01;
(Continued)

(56) References Cited

U.S. PATENT DOCUMENTS

| 4,829,989 | A |   | 5/1989  | Deamer                     |
|-----------|---|---|---------|----------------------------|
| 5,259,833 | A | * | 11/1993 | Barnett .......... A61F 5/026 2/44 |

(Continued)

FOREIGN PATENT DOCUMENTS

DE         196 52 416 A1    6/1998

OTHER PUBLICATIONS

International Preliminary Report on Patentability for International Application No. PCT/NL2016/050170 issued by the European Patent Office, dated Mar. 24, 2017; 6 pages.

*Primary Examiner* — Victoria J Hicks
(74) *Attorney, Agent, or Firm* — Nixon Peabody LLP (57) ABSTRACT

Wearable support structure assists in at least partly relieving a human body during leaning or bending over includes a frame. The frame has a chest support for bearing upon a chest of the human body, pivoting arrangements for pivoting the support structure in correspondence with the leaning or bending or the human body, and two elongated stays connected to the chest support. The stays extend substantially alongside opposite sides of the human body and connect to the pivoting arrangements. stays are resilient stays arranged such that they are in a stretched state corresponding with an upright position of the human body when being unloaded, and arranged to be biased back to the stretched state when being bent into a bent state corresponding with a leaning or bending position of the human body. The structure further includes a lumbar support and a thigh support.

12 Claims, 9 Drawing Sheets

(58) Field of Classification Search
CPC .... A61F 5/00; A61F 5/04; A61F 5/042; A61F 5/048; A61H 3/00; A61H 1/0292; A61H 3/008; A61H 1/0218; A61H 2003/007
USPC .......................................................... 601/5
See application file for complete search history.

(56) References Cited

U.S. PATENT DOCUMENTS

| | | | |
|---|---|---|---|
| 8,657,769 B2* | 2/2014 | Ingimundarson | A61F 5/024 602/19 |
| 2003/0220594 A1 | 11/2003 | Halvorson | |
| 2008/0161738 A1 | 7/2008 | Giesen | |
| 2008/0228121 A1 | 9/2008 | Hughes | |
| 2010/0069806 A1* | 3/2010 | Jinright | A61F 5/01 602/19 |
| 2014/0074003 A1* | 3/2014 | Monden | A61F 5/026 602/19 |
| 2016/0206498 A1* | 7/2016 | Kazerooni | A61F 5/028 |

* cited by examiner

WEARABLE SUPPORT STRUCTURE FOR AT LEAST PARTLY RELIEVING A HUMAN BODY DURING LEANING OR BENDING OVER

CROSS-REFERENCE TO RELATED APPLICATION

This application is a national stage of Application No. PCT/NL2016/050170 filed Mar. 10, 2016, which claims priority from Netherlands Application No. 2014451 filed Mar. 13, 2015, which are both incorporated by reference in their entireties.

The present invention relates to a wearable support structure for at least partly relieving a human body during leaning or bending over, said structure comprising a frame having:

a chest support for bearing upon a chest of said human body;

pivoting arrangements for pivoting the support structure in correspondence with the leaning or bending or the human body;

two elongated stays connected to said chest support, provided to extend substantially alongside opposite sides of said human body and connected to said pivoting arrangements, wherein the stays are resilient stays arranged such that they are in a stretched state corresponding with an upright position of said human body when being unloaded, and arranged to be biased back to said stretched state when being bent into a bent state corresponding with a leaning or bending position of said human body, a lumbar support, connected to said pivoting arrangements, and arranged for bearing upon a lumbar area of said human body, and a thigh support, connected to said pivoting arrangements, and arranged for bearing upon a front side of a thigh area.

International patent application nr PCT/NL2014/050646 discloses such a wearable support structure. One of the downsides of such a wearable support structure is that the human body is relieved during bending over, i.e. from moving the upper body in an upright position to a bended position in a forward direction, and is restricted in its other movement directions. In other words, the known wearable support structure is not efficiently able to provide a supporting, facilitating or a relieving function in other directions of the human body, especially the human torso.

The user thus does not have a relatively large freedom of movement when wearing the known wearable support structure. The load of at least a part of the upper body of the user is supported when bending over, the known support structure is even counter productive for other directions in which the upper body may move, for example laterally. Further, although the resilient stays may facilitate the user to twist his body about its longitudinal axis to a certain extent, this twisting movement may not be perceived as pleasant by the user.

As such, a user wearing the known wearable support structure may feel hindered or restricted in the movement of especially their upper body.

It is therefore an object of the present invention to provide for a wearable support structure which is able to support more freedom of movement for a user, while providing support while leaning forward or bending over, but also during squatting, reaching, crawling, or working from on your knees.

The object is achieved, in a first aspect, in that said chest support comprises two spatially separated pivoting means, wherein said stays are each connected to said chest support via a different one of said pivoting means, wherein each of said pivoting means is arranged to pivot said chest support with respect to a stay connected thereto in a plane substantially parallel to said chest of said human body.

By making the chest support pivotable with respect to a stay connected thereto, it is facilitated that a user wearing the structure has a large freedom of movement. More specifically, the upper body of the user, i.e. the human torso, is for example able to freely move laterally/sideways.

A user wearing the wearable support structure thus has more freedom in their lateral movement, as the lateral movement is supported by the pivoting means in combination with the chest support.

The advantage of the wearable support structure according to the present invention is that it better facilitates a twisting and bending over movement, or a bending and then a twisting movement, of the human body.

Another advantage of the present invention is that, in case a user bends to the left, the chest support turns away from the right shoulder or armpit. This is advantageous as the right arm can then be used to reach to the left without the chest support being in the way. The same is of course true when the user bends to the right, but then vice versa.

The combination of the chest support, the two elongated stays and the pivoting arrangements in fact resembles a part of a parallelogram, wherein the stays and the chest support can move in a plane defined by the parallelogram and with respect to the pivoting arrangements.

The stays are thus arranged such that when the user wearing the support structure bends forwardly from his upright position towards a position including a first angle, the resilient stays also provide for a biasing moment, biasing the resilient stays back to the stretched state of the stay. This thus also provides for a relieving function of the user in other directions than merely the forward bending direction.

In an example, the two elongated stays are rotatably connected to said pivoting arrangements such that the connecting ends of each of said elongated stays is rotatable around its elongated axis.

Typically, a user will not only just bend forward or just lean sideways but their movement will consist of a combination of directions. It is often a combination of a rotation, for example a trunk rotation, and a bending aspect.

By rotatably connecting the connecting ends of each of the elongated stays to the pivoting arrangements, the rotating movement of the torso of the user, i.e. the trunk rotation, is more efficiently supported.

To put it differently, the connecting ends rotate around a vertical axis, which runs from the top to the bottom of the human body. For example, when a gymnast performs a three hundred and sixty degree turn, they're rotating around the vertical axis.

According to the present invention, relieving a human body during bending means that the lower back, i.e. muscles and vertebrae, or the back strain or the body weight forces are reduced.

In the context of the present invention, the lumbar support may be arranged for support a lower end of the back of a human, or even a part of the sacrum area. In a further example, said chest support comprises:

a supporting link having said two spatially separated pivoting means, and a chest bearing support for bearing upon said chest of said human body, wherein said supporting link and said chest bearing support are rotatably connected to each other for rotating said chest bearing support with respect to said connected supporting link in said plane substantially parallel to said chest of said human body.

It was the insight of the inventors that the part of the chest support which is contact with the chest, i.e. which is placed against the chest of a user for supporting at least a part of the load of an upper body should not move against the human body to prevent any high shear forces on the skin. The chest support should thus not slide over, or rotate against the human body as this may feel unpleasant to the user.

The inventors found a solution to the above by dividing the chest support in two different parts.

A first part, i.e. the supporting link, comprises the two spatially separated pivoting means, wherein said stays are each connected to said supporting link via a different one of said pivoting means, wherein each of said pivoting means is arranged to pivot said supporting link with respect to a stay connected thereto in a plane substantially parallel to said chest of said human body.

A second part, i.e. the chest bearing support, is the part which is to be arranged against the chest. The first part and the second part are then rotatably connected to each other, such that the first part and the second part are able to rotate with respect to each other in a plane substantially parallel to the chest of the human body.

Every time a person leans sideways or twists, the second part, i.e. the chest bearing support, will not rotate against the human body thereby preventing any irritation. The rotating movement is supported by the supporting link, and the rotatable connection between the supporting link and the chest bearing support ensure that the chest bearing support does not rotate along with the supporting link. Again, the above mentioned rotating movement is oriented in the plane substantially parallel to the chest of the human.

When a user leans sideways, for example to the left, the supporting link will automatically move away from the right shoulder, thereby creating room for the right arm to reach to the left.

To put it differently, the first part is able to rotate with respect to the second part over an antero posterior axis, which runs from the front to the back of the human body. For example, when a gymnast performs a cartwheel they have rotated around the antero posterior axis.

In a preferred embodiment the supporting link comprises a supporting link having said two spatially separated pivoting means, and a chest bearing support for bearing upon said chest of said human body, wherein said supporting link comprises two substantial parallel links, rotatably connected to the chest bearing support, wherein the supporting link further comprises said two spatially separated pivoting means, wherein a respective pivoting means is rotatably connected to each of the two substantial parallel links. Such a linkage system is advantageous for maintaining the chest bearing support substantially stationary against the human body upon use.

Herewith it is advantageous if said chest support comprises a first part and a second part, wherein said first part is removably connected to said second part, wherein each part comprises a different one of said two spatially separated pivoting means. It was the insight of the inventors that it should be made easy to put the wearable support structure on, and to take the wearable support structure off. The inventors found a solution to the above by construing the chest support as two connectable parts, which parts may be removed from each other, such that both parts can easily be taken off laterally, i.e. sideways.

In an example, the frame further comprises shoulder bands to be placed over the shoulders of said human body, and connect to said chest bearing support for retaining said chest bearing support to said chest of said human body.

The advantage hereof is that the chest support, and thus also the wearable support structure as a whole, is not able to fall down or to move over the body of the human, i.e. the chest support is kept in place against the chest of the human body. In other words, the chest support is retained in its place against the chest of a human body, such that they counteract sliding down of the wearable support structure.

In another example, the supporting link and said chest bearing support are pivotally connected to each other for pivoting around a pivoting axis, said pivoting axis oriented in said plane substantially parallel to said chest of said human body.

Thus, the pivoting axis may be in the direction of the transversal axis, which runs from side to side of the human body. For example, a somersault is a rotation over the transverse axis.

The advantage hereof is that it enables a further degree of freedom in which a user is able to move its upper body without feeling any hinder or the like as this ensures that the supporting link pivots with respect to the chest bearing support to compensate for the bending position of the human or the angular position of the chest of the human.

In a further example, said chest bearing support comprises a cushion part for bearing upon said chest of said human body, wherein a shape, or orientation, of said cushion part substantially is substantially tailored to said chest for setting a pivoting position of said supporting link to said chest bearing support. For example, the cross sectional view, i.e. cross section in the sagittal plane, of the cushion part may resemble a wedge shape for adjusting for a particular shape of a chest.

The advantage hereof is that, initially, the wearable support structure, more specifically the chest support is adjusted to the shape of the chest of a human, such that the chest support is aligned in the plane substantially parallel to the chest of a human.

In another example, said supporting link and said chest bearing support are rotatably connected to each other for rotating said chest bearing support with respect to said connected supporting link in said plane substantially parallel to said chest of said human body around a sagittal axis, said supporting link comprising a first part removably connected to a second part, wherein said first part is rotatably connected to a corresponding first part of said chest bearing support over a first axis, and said second part is rotatably connected to a corresponding second part of said chest bearing support over a second axis, wherein said first axis and said second axis coincide when said first part and said second part, and thus also the first part of said chest bearing support and said second part of said chest bearing support, connect.

It was the insight of the inventors that it should be made easy to put the wearable support structure on, and to take the wearable support structure off. The inventors found a solution to the above by construing the supporting link as two connecting parts, which parts may be removed from each other, such that both parts can easily be taken off laterally, i.e. sideways.

One of the advantage of the wearable support structure of the present invention is that the chest support may be arranged in a thin manner, i.e. the thickness of the chest support may be made small. This has the advantage for a user as the chest support looks more elegant and is more comfortable to wear.

In case the wearable support structure comprises two shoulder bands, the two shoulder bands are then to be placed over the shoulders of said human body, and each connect to one of said first and said second part of said chest bearing support for retaining said chest bearing support to said chest of said human body. The advantage hereof, is that the wearable support structure can be taken of just like a coat or the like.

The shoulder bands are further connected to the pivoting arrangements, such that the weight of the wearable support structure is facilitated via the pivoting arrangement and the shoulder bands to the shoulders of the human. The shoulder bands may further comprise provisions for setting the length of the bands such that the length of the bands may be tailored to the length of the upper body of the user.

In an even further example, said first and said second part each comprise a half-arc-shaped rail construction for providing said pivoting connection to said chest bearing support in said plane substantially parallel to said chest of said human body, wherein said half-arc-shaped rail constructions form a full-arc-shaped rail construction when said first part and said second part are connected, wherein a center of said full-arc-shaped rail construction coincides with said sagittal axis.

In another example, the chest support comprises recesses and/or ribs or corrugations for removing said first part of said supporting link and said first part of said chest bearing support from said second part of said supporting link and said second part of said chest bearing support.

In an example, the first part of said chest bearing support comprises connecting receiving means, and wherein said second part of said chest bearing support comprises a connecting protrusion element arranged for receiving, and locking, in said connecting receiving means.

In a detailed example, the frame comprises two shoulder bands to be placed over shoulders of said human body, wherein a first shoulder band is connected to a first part of said chest bearing support, and a second shoulder band is connected to a second part of said chest bearing support, for retaining said chest bearing support to said chest of said human body.

The advantage hereof, is that the wearable support structure can be taken of, just like a coat or the like.

In a further example, the lumbar support is pivotally connected to said pivoting arrangements, for pivoting said lumbar support with respect to said pivoting arrangements around a lumbar axis, said lumbar axis oriented substantially horizontally in said plane substantially parallel to said chest of said human body.

The advantage hereof is that the lumbar support is kept better on its place during, for example, a bending movement by the user.

In yet another example, each of said pivoting movements are limited in their pivoting range such as to prevent said wearable support structure to get entangled.

The pivoting movements comprised by the wearable support structure are thus limited in their range, i.e. in the amount in which they are able to pivot. The main benefit hereof is that the wearable support structure can not get entangled when the wearable support structure is stored.

In an example, said pivoting arrangements further comprise a counter for tracking a number of bends made by the wearable support structure.

This may be beneficial for proving the amount of bends made using the wearable support structure.

Typically, the length of said supporting link is between 100 mm and 300 mm, preferably between 100 mm-200 mm, even more preferably around 150 mm.

The inventors found that the length of the supporting link, which is, in use, the length of the supporting link in the shoulder-to-shoulder direction, is related to the length and flexibility of the chest of a human, which length is in vertical direction of the user. Typically, the length should be around 150 mm to obtain the best results for the wearable support structure.

In the context of the present invention, an upright position of a body is to be understood as meaning a position in which the trunk or torso of the body is substantially directly vertically above the hips and/or legs. A stretched state is to be understood as substantially a position in which the at least one stay will be in when the stay is not externally loaded by an force, or at least not externally loaded by any force other than a force clamping the stay to the human body when in the upright position.

In the context of the present invention, supporting is to be understood as providing a force sufficient to support part of the weight of the upper body when moved away from the straight, upright body position in any direction.

The expressions, i.e. the wording, of the different aspects comprised by the wearable support structure according to the present invention should not be taken literally. The wording of the aspects is merely chosen to accurately express the rationale behind the actual function of the aspects.

In The above-mentioned and other features and advantages of the invention will be best understood from the following description referring to the attached drawings. In the drawings, like reference numerals denote identical parts or parts performing an identical or comparable function or operation.

The invention is not limited to the particular examples disclosed below in connection with a particular type of wearable support structure.

Figure 1:
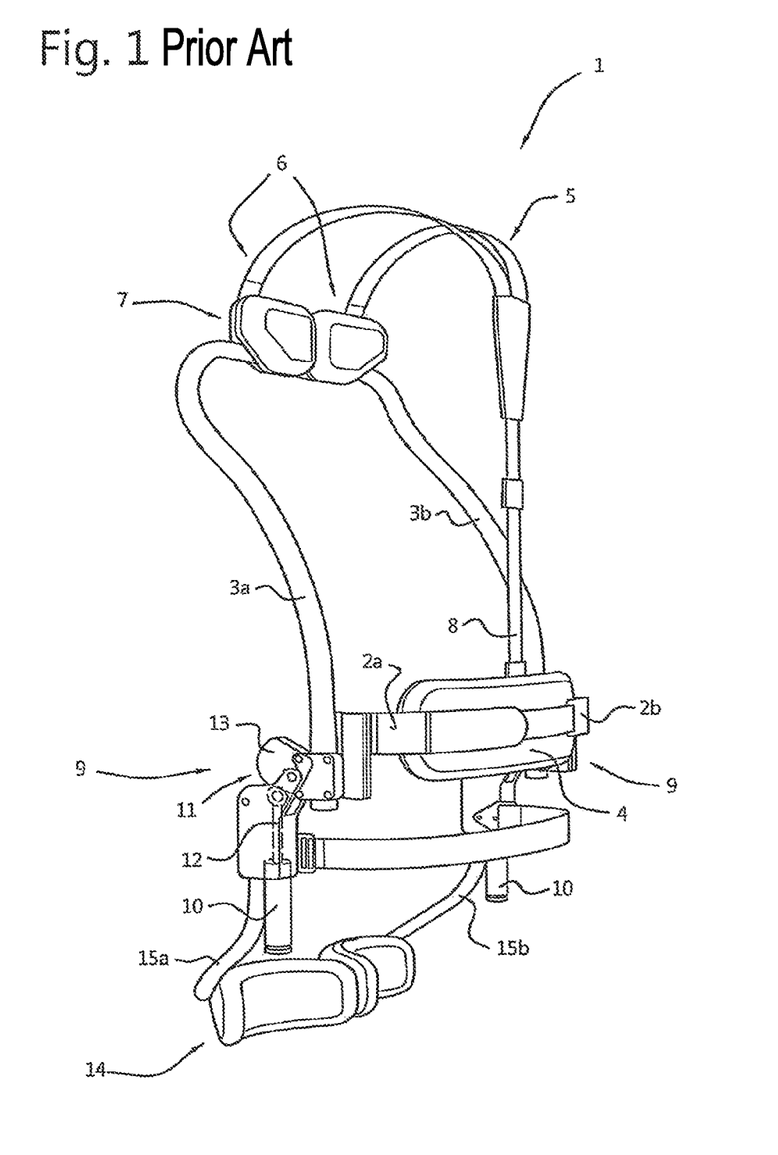
FIG. 1 is a view of a known wearable support structure.

FIG. 1 is a view of a known wearable support structure 1, which comprises substantially rigid arms 2a, 2b connected to the stays 3a, 3b, respectively. The arms 2a, 2b are positioned such as to be directed towards the spinal column of a user during use. The lumbar support 4 is connected to the stays 3a, 3b to support the lumbar during use.

The known structure may further comprise one or more shoulder bands 5 or braces 5. The shoulder bands 5 may be resilient and/or can at least partly be formed by means of an elastic band. The one or more shoulder bands 5 or braces 5 may counteract sliding down of the wearable support structure 1.

Here, first ends 6 of the shoulder bands 5 connected to the chest support 7, which chest support is arranged to be retained against the chest of a human body. A second end 8 of the shoulder bands 5 is connected to the lumbar support 4.

The wearable support structure further comprises pivoting arrangements 9 comprising biasing means such that, during use, the stays 3a, 3b are biased towards a stretched state corresponding with an upright position of the human body. The pivoting arrangements 9 further comprise a compression spring 10 or a gas spring 10. The compression spring 10 or gas spring 10, which has a substantially linear spring characteristic, cooperates with a cam surface 11. The cooperating cam surface 11 and gas spring 10 are arranged such that when the upper and lower stay parts are pivoted around the pivot axis 13 from a stretched position towards a position including a first angle, the pivoting arrangements 9 provide for an increasing biasing moment which biases the stay back to the stretched position and when pivoting further around said pivot axis 13 from the said angle the biasing moment is substantially maintained or decreases.

The wearable support structure, more specifically the frame thereof, comprises a thigh support 14, connected to the pivoting arrangements 9 via lower stays 15a, 15b, is arranged for bearing upon a lumbar area of the human body.

Figure 2:
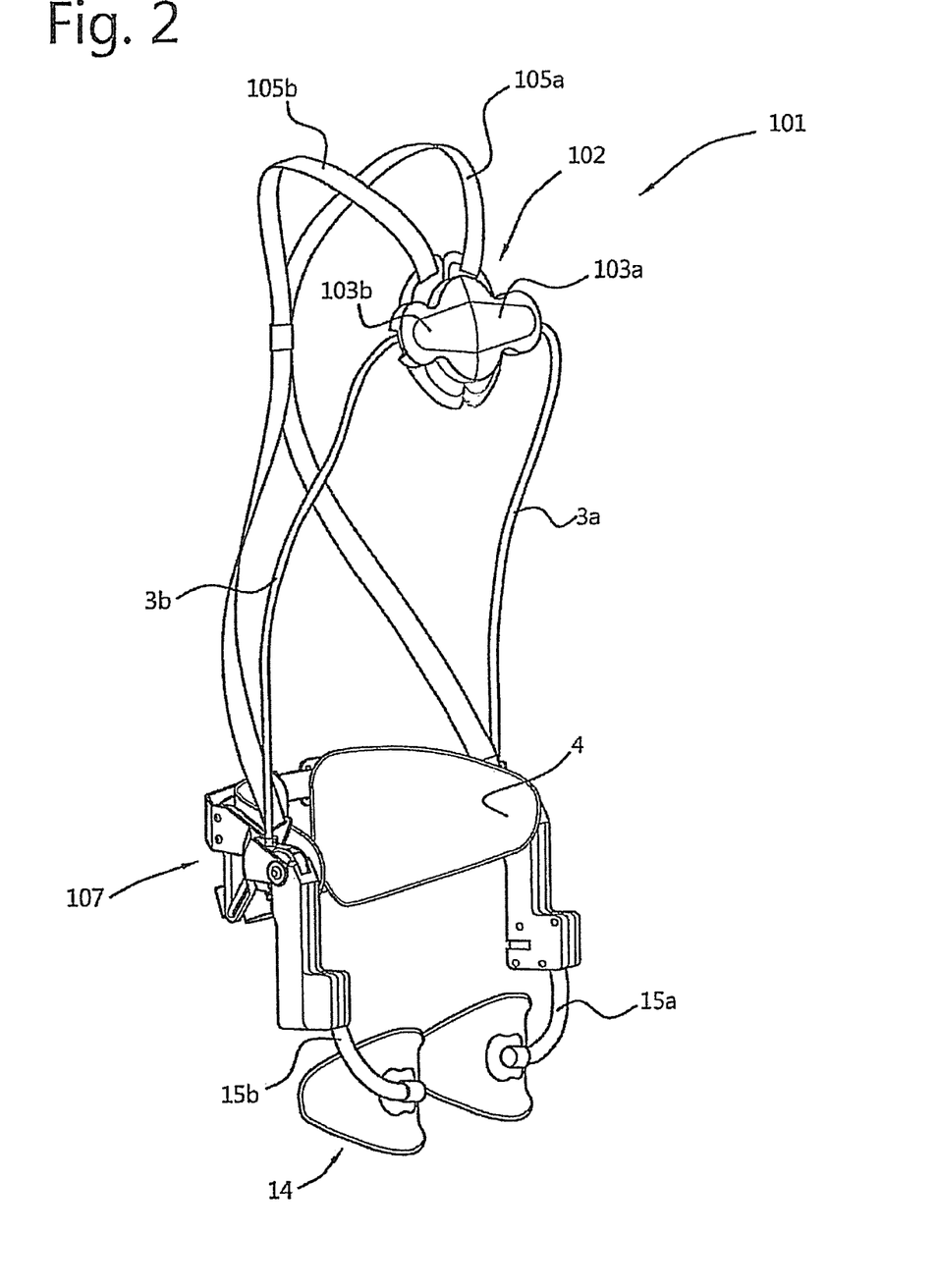
FIG. 2 is a view of a wearable support structure according to the present invention.

FIG. 2 is a view of a wearable support structure 101 according to the present invention.

The wearable support structure 101 is arranged for at least partly relieving a human body during leaning or bending over in any direction. The improved support structure 101 thus also provides for more freedom of motion in all directions, and provides for a relieving function in twisted bending.

The support structure 101 comprises a frame having a chest support 102 for bearing upon a chest of said human body, which chest support 102 will be explained in more detail further below.

Pivoting arrangements 107 are provided for pivoting the support structure in correspondence with the leaning or bending or the human body.

The frame further comprises two elongated stays 3a, 3b connected to the chest support 102, which stays 3a, 3b are provided to extend substantially alongside opposite sides of the human body and connect to the pivoting arrangements 107.

According to the present invention, the stays 3a, 3b are resilient stays arranged such that they are in a stretched state corresponding with an upright position of said human body when being unloaded, and arranged to be biased back to said stretched state when being bent into a bent state corresponding with a leaning or bending position of the human body.

The stays 3a, 3b may be substantially strip shaped, having a three-dimensional curved shape, the strip having for example a flat, curved, triangular or multi angular, round or oval cross section, which may be constant over the length of the stay or can vary along its length.

The frame further comprises a lumbar support 4, connected to said pivoting arrangements, and arranged for bearing upon a lumbar area of said human body, and comprises a thigh support 14, connected to said pivoting arrangements via lower stays 15a, 15b, and arranged for bearing upon a front side of a thigh area.

The invention is characterized in that said chest support 102 comprises two spatially separated pivoting means, wherein said stays 3a, 3b are each connected to said chest 102 support via a different one of said pivoting means, wherein each of said pivoting means is arranged to pivot said chest support 102 with respect to a stay 3a, 3b connected thereto, in a plane substantially parallel to said chest of said human body. The chest support 102 is in more detailed explained in correspondence with FIGS. 3 and 4.

Shoulder bands 105a, 105b are provided, which shoulder bands 105a, 105b are to be placed over shoulders of said human body, and to be connected to the chest support 102 for retaining said chest support 102 to the chest of the human body.

The inventors further found an improved method for manufacturing of the stays 3a, 3b. The stays 3a, 3b are manufactured such that the shape thereof is tailored to the body of a human. However, both ends of the stays are, typically, substantially straight, and too long. For each human body, or for certain length types of the human body, the ends of the stays 3a, 3b may be cut to correct size. The advantage hereof is that during the manufacturing process, only one type of stays 3a, 3b may be produced, which manufactured stays 3a, 3b may then, subsequently, be cut to the correct size.

Further, the pivoting arrangements 107 may be provided with a counter (not shown) which digitally, or analogously, keeps track of the number of bends made by the user. This may be beneficial for proving the amount of bends made using the wearable support structure.

Figure 3:
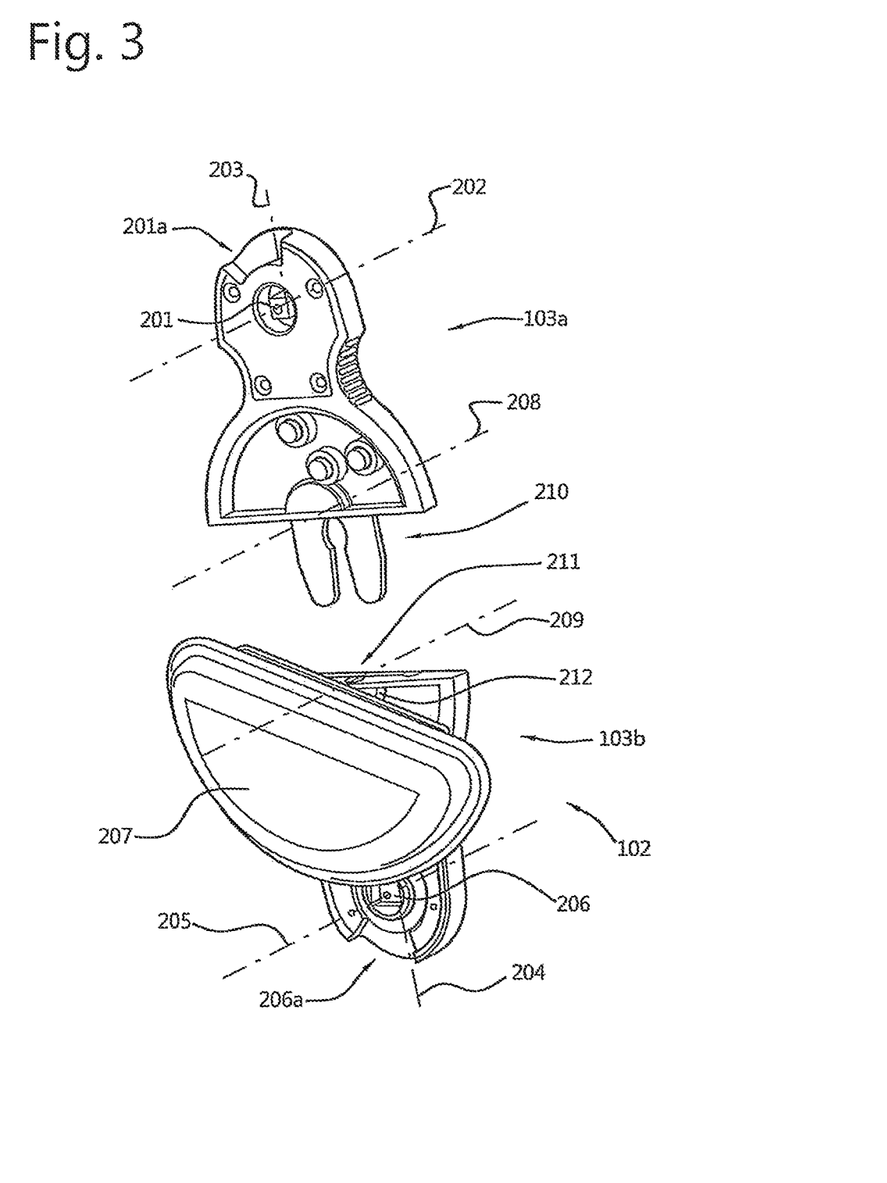
FIG. 3 is a view of an example of a chest support comprised in the wearable support structure according to the present invention.

FIG. 3 is a view of an example of a chest support 102 comprised in a wearable support structure according to the present invention.

Here, the chest support 102 comprises a supporting link in the form of a first part 103a and a second part 103b, and a chest bearing support 207 for bearing upon the chest of the human body. Here, only one rotating part of the chest bearing support 207 is shown.

The first part 103a comprises the first pivoting means 201 and the second part 103b comprises the second pivoting means 206. The first stray 3a is to be connected to the first pivoting means 201 via the first receiving opening 201a. The second stray 3b is connected to the second pivoting means 206 via the second receiving opening 206a.

The pivoting means 201, 206 are spatially separated in that the first pivoting means 201 are located at a first side of the supporting link, and the second pivoting means 206 are located at a second, opposing, side of the supporting link.

The pivoting means are each arranged to pivot said chest support 102 with respect to a stay connected thereto, in a plane substantially parallel to the chest of the human body. In the present example, this is indicated with the first axis 202, which first axis 202 is orthogonal to the above mentioned plane.

As mentioned above, the chest bearing support 207 is intended to be placed against a human body. In order to increase the comfort for a user, the chest bearing support 207 may comprise a cushion part (not shown) for bearing upon said chest of said human body, wherein a shape of said cushion part substantially resembles a wedge shape tailored to said chest for setting a pivoting position of said supporting link to said chest bearing support 207.

The supporting link, i.e. in the form of the first part 103a and the second part 103b, is pivotally connected to the stays 3a, 3b receiving in the receiving openings 206a, 201a, wherein the pivoting axis 203, 204 is oriented in said plane substantially parallel to said chest of said human body. This pivoting connection is, in the present example, also provided by the pivoting means 201, 206.

In accordance with the present invention, the supporting link 103a, 103b and the chest bearing support 207 are rotatably connected to each other for rotating said chest bearing support respectively to said connected supporting link in said plane substantially parallel to said chest of said human body.

In order to accommodate the above mentioned rotating movement between the chest bearing support 207 and the supporting link 103a, 103b, as well as to accommodate that the first part 103a is to be removably connected to a second part 103b, the inventors came up with an inventive concept which is explained in more detail below.

The first part 103a and the second part 103b each comprise a half-arc-shaped rail construction 212 (only one rail is shown) for providing the rotating connection to the chest bearing support 207 in the plane substantially parallel to said chest of said human body. Of course, the half-arc-shaped rail construction 212 may also be provided in the chest bearing support 207 in stead of in the first part 103a and the second part 103b, respectively.

The idea hereof is that both half-arc-shaped rail constructions 212, i.e. the one present on the first part 103 and the one present on the second part 103b, form a full-arc-shaped rail construction when said first part 103a and said second part 103b are connected.

The half-arc-shaped rail construction 212 of the second part 103b rotates over a second axis 209, and the half-arc-shaped rail construction (not shown) of the first part 103b rotates over a fifth axis 208, wherein, when the first part 103a and the second part 103b are connected to each other, the second axis 209 and the fifth axis 208 coincide with each other such that the complete construction, i.e. the chest bearing support 207 is able to rotate with respect to the supporting link, i.e. the first part 103a connected to the second part 103b.

Figure 4:
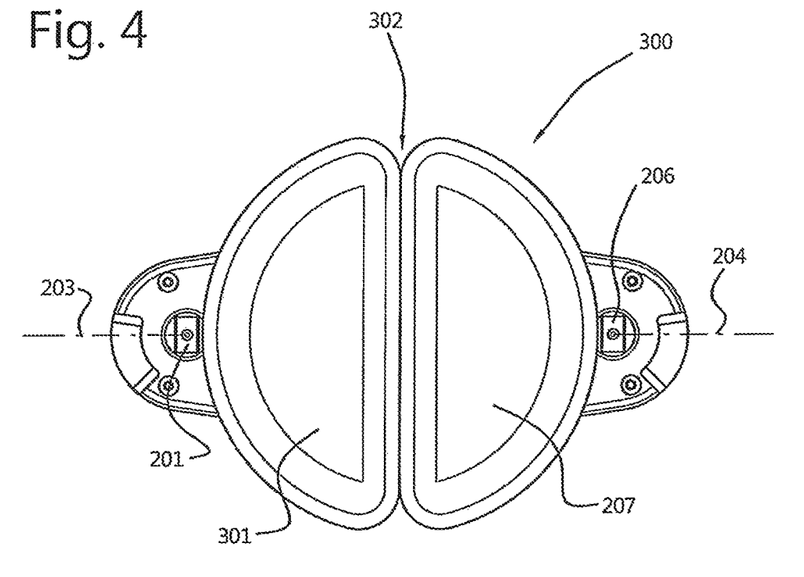
FIG. 4 is another view of an example of a chest support comprised in the wearable support structure according to the present invention.

FIG. 4 is a view of an example of a chest support 300 comprised in a wearable support structure according to the present invention.

Here, it is shown that the first part 103a is connected to the second part 103b such that the supporting link is formed. The supporting link can thus be disassembled via the disassembling axis 302, such that the first part 103a is free from the second part 103b as is shown in FIG. 3.

The chest bearing support is indicated with reference numeral 207 and with reference numeral 301.

The first pivoting means 201 connect to the first stay 3a, which first stay 3a is received via the first receiving opening 201a. The second pivoting means 206 connect to the second stay 3b, which second stay 3b is received via the second receiving opening 206a.

In an example of the present invention, both the pivoting means 201, 206, are arranged to pivot the stays 3a, 3b, respectively, with respect to the chest support 300 around the fourth axis 204 and the second axis 203, respectively.

Figure 5:
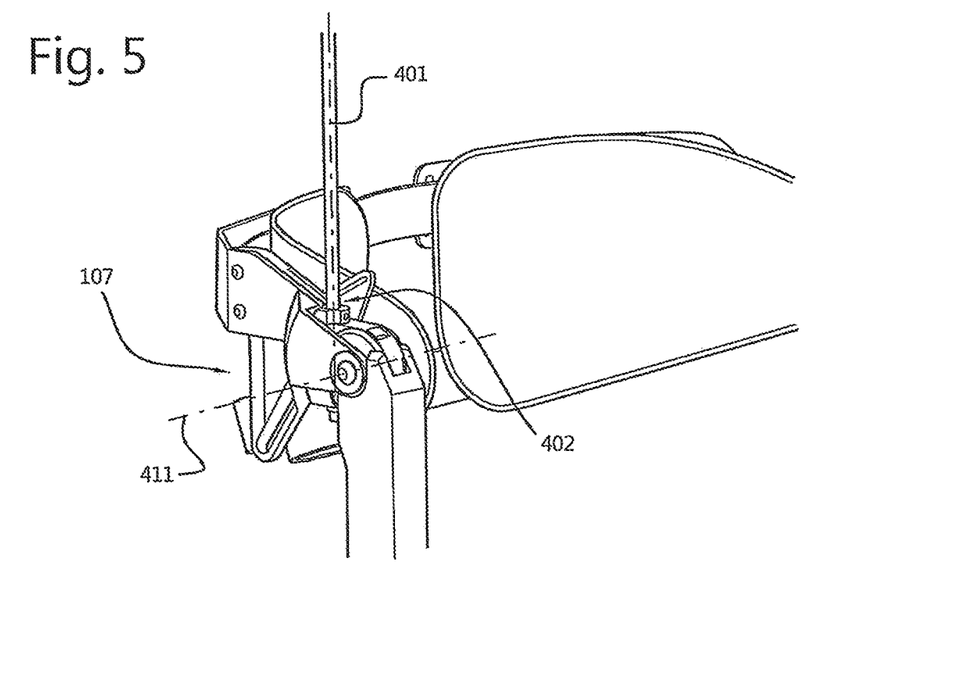
FIG. 5 is a view disclosing an example of a pivoting arrangement comprised in the wearable support structure according to the present invention.

FIG. 5 is a view disclosing an example of a pivoting arrangement 107 comprised in the wearable support structure according to the present invention.

Here, the first stay 3a is connected to the pivoting arrangement 107 such that the connecting end 402 of each the first stay 3a is rotatable around its elongated axis 401. The lumbar support is pivotally connected to said pivoting arrangements 107, for pivoting said lumbar support with respect to said pivoting arrangements 107 around a lumbar axis 411, said lumbar axis 411 oriented substantially horizontally in said plane substantially parallel to said chest of said human body.

Figure 6:
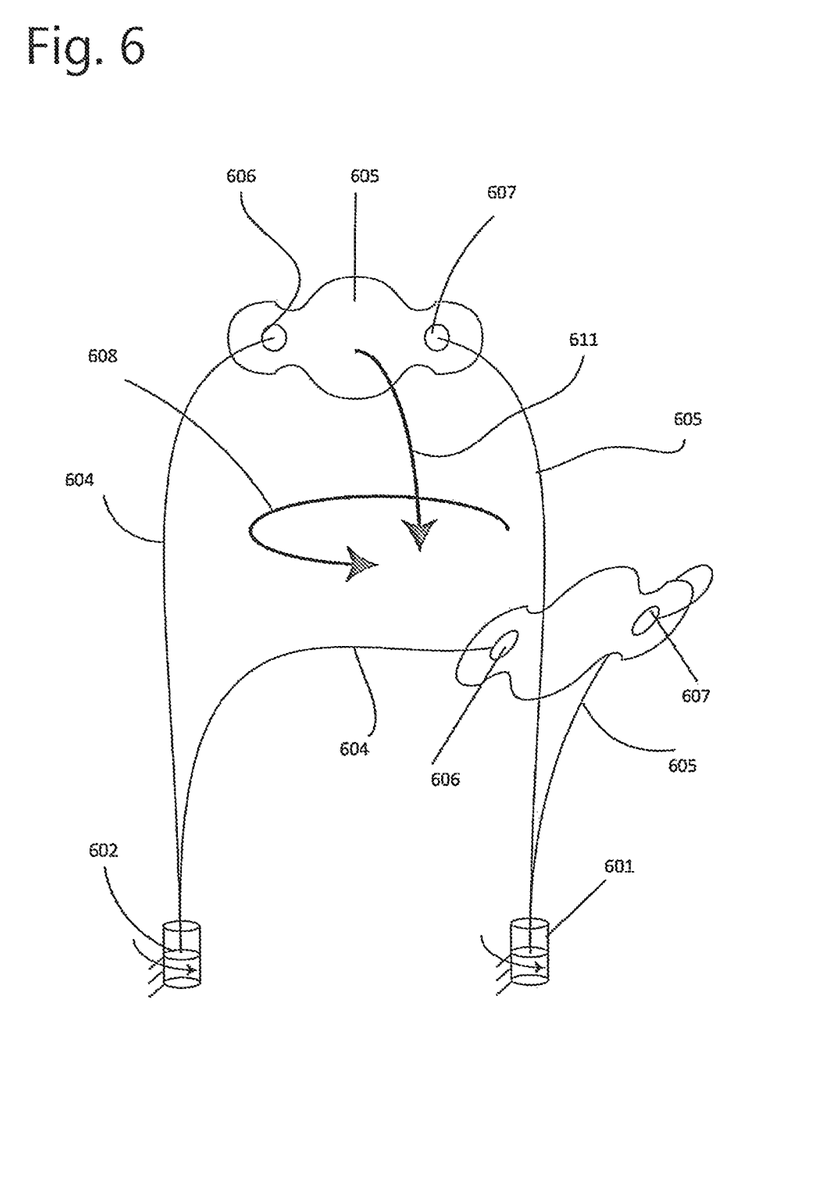
FIG. 6 is a very schematic view of pivoting arrangements, stays and a chest wearing support, according to the present invention. Here, a twisting and bending movement of the user is displayed.

FIG. 6 is a very schematic view of pivoting arrangements 601, 601, stays 603, 604 and a chest bearing support 605, according to the present invention. The principle shown here is that the user twists around its vertical axis 608, and bends forward 611.

Here, the principle working of the pivoting means 606, 607 comprised by the chest bearing support 605 is displayed in a bit more detail. In the initial state, i.e. the upright position, the chest bearing support 605 is located against the chest of the human body. Once the user move twists, i.e. rotates along its vertical axis, and bends, the chest support 605 will follow the chest of the human. In other words, the chest support 605 facilitates this movement of the upper body of the human. This is facilitated by the pivoting means 606, 607, as these pivoting means 606, 607 are arranged to pivot the corresponding stay 603, 604, with the chest bearing support 605.

The twisting movement of the user is further support by the rotating connection of the stays 603, 604 in the pivoting arrangements 601, 602. This rotating connection, i.e. twisting movement, is indicated with reference numeral 608. The ends of the stays 603, 604 are thus rotatably connected in the corresponding pivoting arrangements 601, 602.

Figure 7:
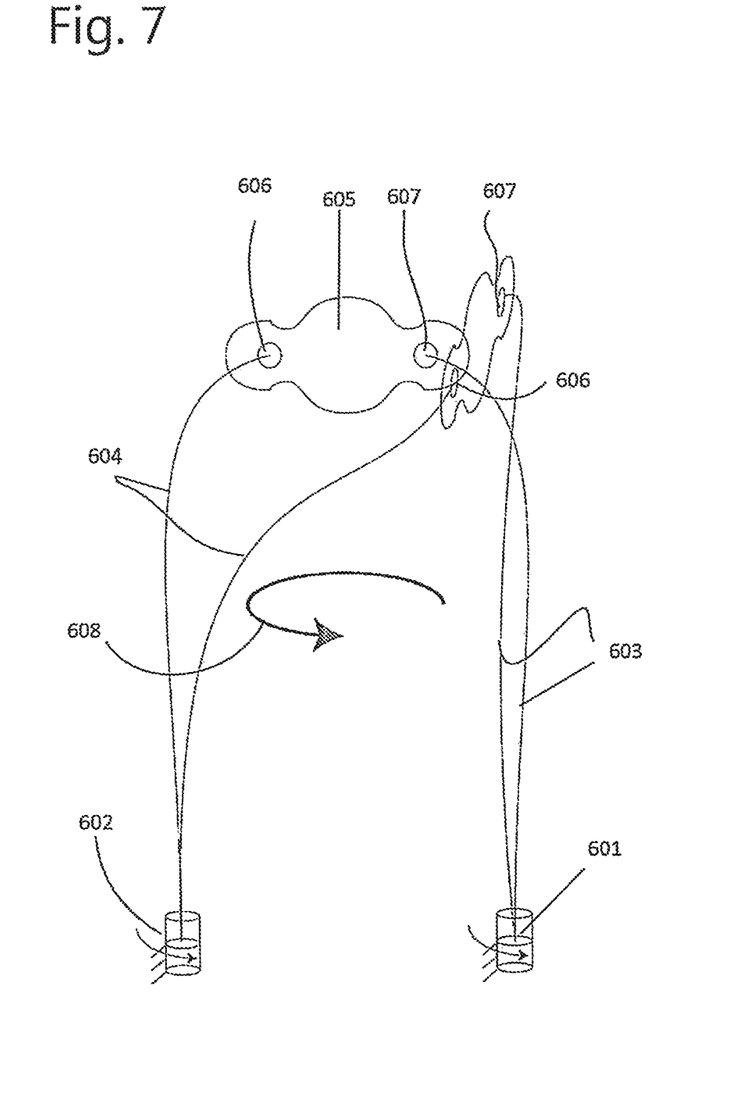
FIG. 7 is a very schematic view of pivoting arrangements, stays and a chest wearing support, according to the present invention. Here, a twisting movement of the user is displayed.

FIG. 7 is a very schematic view of pivoting arrangements 601, 601, stays 603, 604 and a chest bearing support 605, according to the present invention. Here, the same layout is provided as provided in FIG. 6. The difference is that here only a twisting 608 movement of the user is shown in stead of a twisting and a bending movement as compared to FIG. 6.

Figure 8:
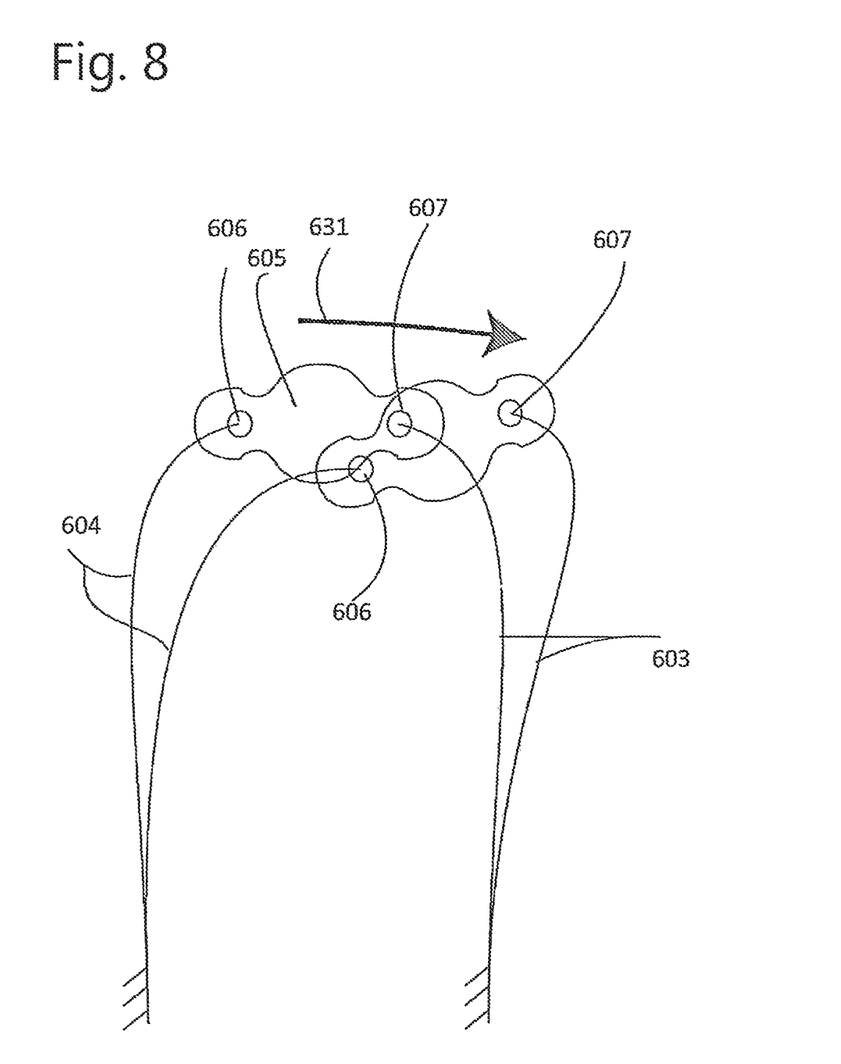
FIG. 8 is a very schematic view of pivoting arrangements, stays and a chest wearing support, according to the present invention. Here, a lateral movement of the user is displayed.

FIG. 8 is a very schematic view of pivoting arrangements 601, 601, stays 603, 604 and a chest bearing support 605, according to the present invention. Here, the same layout is provided as provided in FIG. 6 and FIG. 7. The difference is that here only a lateral 631 movement of the user, i.e. a movement sideways, is shown in stead of a twisting and a bending movement as compared to FIG. 6.

Figure 9:
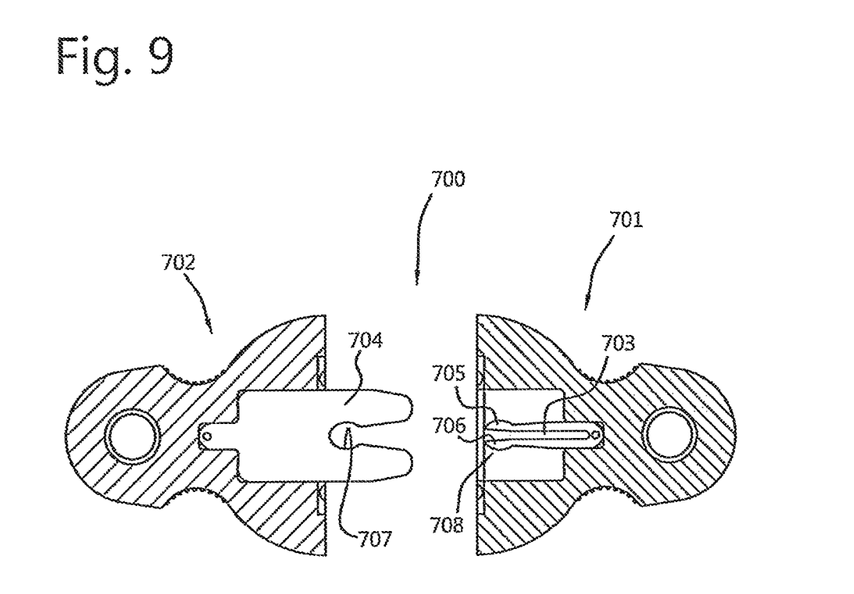
FIG. 9 is a view of a first part of said chest bearing support and a second part of said supporting link, according to the present invention.

FIG. 9 is a view of a first part of said chest bearing support and a second part of said chest bearing support, according to the present invention.

The first part 701 of said chest bearing support 700 comprises connecting receiving means 703, and wherein said second part 702 of said chest bearing support 700 comprises a connecting protrusion element 704 arranged for receiving, and locking, in said connecting receiving means 703.

The connecting receiving means 703 may be construed as two separate, flexible, elements 705, 706, which are able to deform slightly when the protrusion element 704 is pushed against these elements 705, 706. These elements 705, 706 move towards each other such that the protrusion element 704 can be placed over the elements 705, 706.

The round shape 707 of the protrusion element, and the corresponding shape 708 at the elements 705, 706 make sure that the final end between the protrusion element 704 and the elements 705, 706, gets attracted. In other words the elements 705, 706 are drawn into the protrusion element 704, using its round shape 707.

Figure 10:
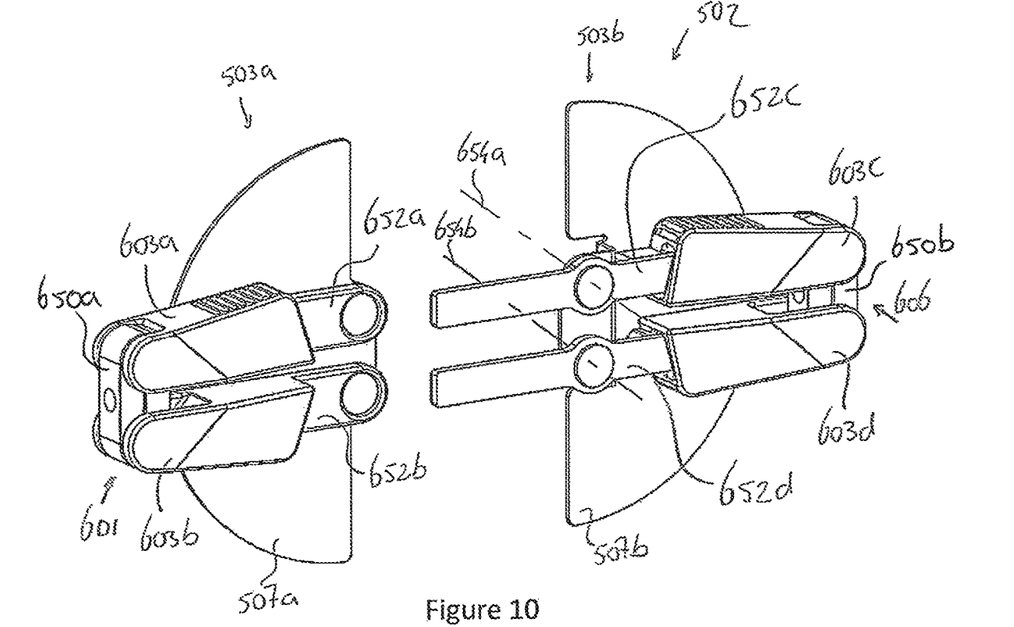
FIG. 10 is a view of an example of a chest support

FIG. 10 is a view of an example of a chest support 502 comprised in a wearable support structure according to the present invention.

Chest support 502 differs mainly from chest support 102 in that the connection between the first pivoting means 601 and the second pivoting means 606 comprise substantially parallel connecting bodies 650a and 650b. Reference numbers of chest support 502 of parts similar to the chest support 102 are raised by 400. The supporting link, i.e. in the form of the first part 503a and the second part 503b, is pivotally connected to the stays 3a, 3b with connecting bodies 650a, 650b. Connecting body 650a is rotatably connected to links 603a and 603b at first ends thereof. Connecting body 650b is rotatably connected to links 603c and 603d at first ends thereof. At second ends thereof the links 603a-d are connected to connecting strips 652a-d. The connecting strips 652a and 652b are rotatably connected to the chest bearing support 507a and configured to connect with the connecting strips 652c and 652d for rotation about pivot axis 654a or 654b. The connecting strips 652c and 652d are rotatably connected to the chest bearing support 507b for rotation about pivot axis 654a or 654b. The links 603a-d and the connecting strips 652a-d together with the bodies 650a-b form a substantially parallel linkage system wherein the bodies 650a-b are kept substantially parallel with respect to each other. Upon use, the chest bearing support 507a-b will not rotate relative to the chest of the human body. Any rotation of the first stray 3a and second stray 3b with respect to the chest support 502 is accommodated by the parallel links 603a-d and connecting bodies 650a-b.

Figure 11:
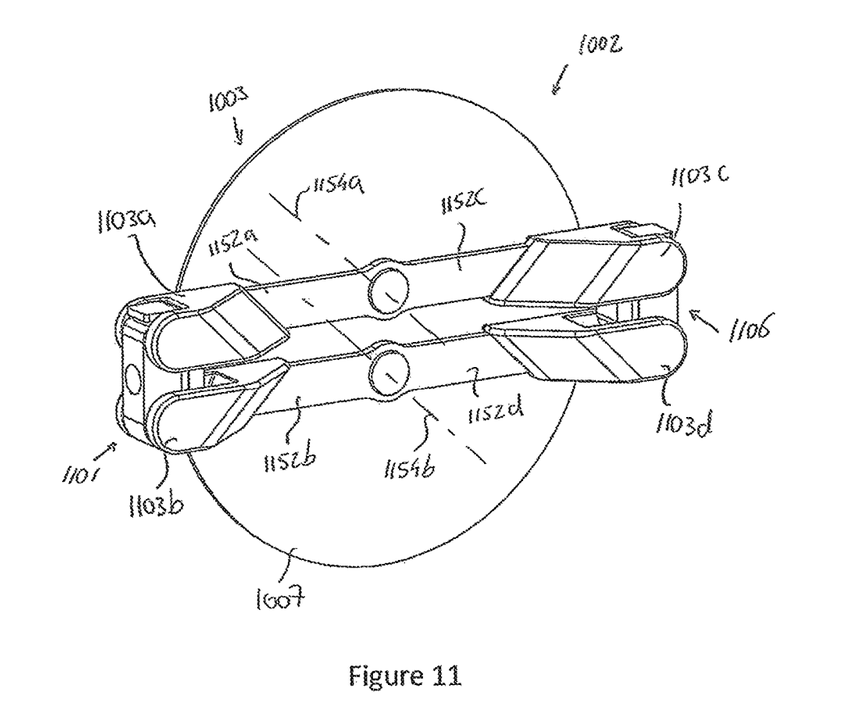
FIG. 11 is a view of an example of a chest support.

FIG. 11 is a view of an example of a chest support 1002 comprised in a wearable support structure according to the present invention. Chest support 1002 differs mainly from chest support 502 in that the supporting link 1003 is in the form of one integral part. Chest support 1002 is not dividable Reference numbers of chest support 1002 of parts similar to the chest support 502 are raised by 500.

The present invention is not limited to the embodiments as disclosed above, and can be modified and enhanced by those skilled in the art beyond the scope of the present invention as disclosed in the appended claims without having to apply inventive skills.

The invention claimed is:

1. Wearable support structure for at least partly relieving a human body during leaning or bending over, said wearable support structure comprising a frame having:
    a chest support for bearing upon a chest of said human body;
    pivoting arrangements for pivoting the wearable support structure in correspondence with the leaning or bending of the human body;
    two elongated stays connected to said chest support, provided to extend substantially alongside opposite sides of said human body and connected to said pivoting arrangements,
    wherein the two elongated stays are resilient stays arranged such that they are in a stretched state corresponding with an upright position of said human body when being unloaded, and arranged to be biased back to said stretched state when being bent into a bent state corresponding with a leaning or bending position of said human body,
    a lumbar support, connected to said pivoting arrangements, and arranged for bearing upon a lumbar area of said human body, and
    a thigh support, connected to said pivoting arrangements, and arranged for bearing upon a front side of a thigh area,
    characterized in that
    said chest support comprises two spatially separated pivoting means, wherein said two elongated stays are each connected to said chest support via a different one of said two spatially separated pivoting means, wherein each of said two spatially separated pivoting means is arranged to pivot said chest support with respect to a respective one of said two elongated stays connected thereto, in a plane substantially parallel to said chest of said human body and
    wherein the two elongated stays are distinct and discrete from the pivoting arrangements.

2. Wearable support structure according to claim 1, wherein said chest support comprises:
    a supporting link having said two spatially separated pivoting means, and
    a chest bearing support for bearing upon said chest of said human body,
    wherein said supporting link and said chest bearing support are rotatably connected to each other for rotating said chest bearing support respectively to said supporting link in said plane substantially parallel to said chest of said human body.

3. Wearable support structure according to claim 2, wherein said frame further comprises shoulder bands to be placed over shoulders of said human body, and connected to said chest bearing support for retaining said chest bearing support to said chest of said human body.

4. Wearable support structure according to claim 3, wherein said frame comprises two shoulder bands to be placed over shoulders of said human body, wherein a first shoulder band of the two shoulder bands is connected to a first part of said chest bearing support, and a second shoulder band of the two shoulder bands is connected to a second part of said chest bearing support, for retaining said chest bearing support to said chest of said human body.

5. Wearable support structure according to claim 2, wherein said supporting link and said chest bearing support are pivotally connected with respect to said two elongated stays around a pivoting axis, said pivoting axis adapted to be oriented in said plane substantially parallel to said chest of said human body.

6. Wearable support structure according to claim 2, wherein a length of said supporting link is between 100 mm and 300 mm.

7. Wearable support structure according to claim 1, wherein said chest support comprises:
    a supporting link having said two spatially separated pivoting means, and
    a chest bearing support for bearing upon said chest of said human body,
    wherein said supporting link comprises two substantially parallel links, rotatably connected to the chest bearing support, wherein the supporting link further comprises said two spatially separated pivoting means, wherein each of the two spatially separated pivoting means is rotatably connected to a respective one of the two substantially parallel links.

8. Wearable support structure according to claim 7, wherein said chest support comprises a first part and a second part, wherein said first part is removably connected to said second part, wherein each part comprises a different one of said two spatially separated pivoting means.

9. Wearable support structure according to claim 1, wherein the two elongated stays are rotatably connected to said pivoting arrangements such that connecting ends of each of said two elongated stays is rotatable around its elongated axis.

10. Wearable support structure according to claim 1, wherein said lumbar support is pivotally connected to said pivoting arrangements, for pivoting said lumbar support with respect to said pivoting arrangements around a lumbar axis, said lumbar axis oriented substantially horizontally in said plane substantially parallel to said chest of said human body.

11. Wearable support structure according to claim 1, wherein each of said two spatially separated pivoting means is limited in their pivoting range such as to prevent said wearable support structure from getting entangled.

12. Wearable support structure according to claim 1, wherein said pivoting arrangements further comprise a counter for tracking a number of bends made by the wearable support structure.

* * * * *